United States Patent
Merkel et al.

(10) Patent No.: US 9,682,917 B2
(45) Date of Patent: Jun. 20, 2017

(54) METHOD FOR TREATING A SUBSTANCE MIXTURE COMPRISING AN AROMATIC AMINE, IN PARTICULAR A SUBSTANCE MIXTURE OF RAW ANILINE

(71) Applicant: Bayer MaterialScience AG, Leverkusen (DE)

(72) Inventors: Michael Merkel, Dusseldorf (DE); Thomas Knauf, Dormagen (DE); Cliff Andre Peters, Schmedeswurth (DE); Thorsten Schmidt, Nindorf (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/397,914

(22) PCT Filed: Apr. 29, 2013

(86) PCT No.: PCT/EP2013/058898
§ 371 (c)(1),
(2) Date: Oct. 30, 2014

(87) PCT Pub. No.: WO2013/164308
PCT Pub. Date: Nov. 7, 2013

(65) Prior Publication Data
US 2015/0094493 A1 Apr. 2, 2015

(30) Foreign Application Priority Data
May 4, 2012 (EP) .................................... 12166832

(51) Int. Cl.
*C07C 209/84* (2006.01)
(52) U.S. Cl.
CPC .................. *C07C 209/84* (2013.01)

(58) Field of Classification Search
None
See application file for complete search history.

(56) References Cited

U.S. PATENT DOCUMENTS

| 5,728,880 A | 3/1998 | Beckhaus et al. |
| 5,808,157 A | 9/1998 | Langer et al. |
| (Continued) | | |

FOREIGN PATENT DOCUMENTS

| JP | 09-241223 | 9/1997 |
| JP | 2005350388 A | 12/2005 |
| JP | 2008266315 A | 11/2008 |

OTHER PUBLICATIONS

Chem. Soc. Rev, 3 (2), pp. 209-(1974)—"Chemistry of the Production of Organic Isocyanates" by H. J. Twitchett.
(Continued)

*Primary Examiner* — Clinton Brooks
(74) *Attorney, Agent, or Firm* — N. Denise Brown

(57) ABSTRACT

The present invention relates to a method for treating a substance mixture comprising an aromatic amine, wherein the aromatic amine is aniline or 2,4-diaminotoluene, preferably aniline. The substance mixture comprises an aromatic amine and compounds having a higher boiling point than the aromatic amine. The method for treating the substance mixture requires I) separating the first substance mixture by means of distillation in a first distillation unit (110, 1130), to at least partially remove some of the aromatic amine in the process, and to obtain a first bottom product which is removed from the first distillation unit (110, 1130). After removal from the first distillation unit (110, 1130), the bottom product is diluted with a condensed top product from a distillation unit that is different from the first distillation unit and/or with a composition that comprises methanol.

9 Claims, 2 Drawing Sheets

(56) References Cited

U.S. PATENT DOCUMENTS

| | | |
|---|---|---|
| 5,877,350 A | 3/1999 | Langer et al. |
| 6,043,394 A | 3/2000 | Langer et al. |
| 6,443,170 B1 | 9/2002 | Vansant et al. |
| 7,253,321 B2 | 8/2007 | Hagen et al. |
| 7,342,134 B2 | 3/2008 | Knoesche et al. |
| 8,295,612 B2 | 10/2012 | Yokoyama |
| 2007/0203364 A1* | 8/2007 | Dugal .................. C07C 209/36 564/423 |
| 2008/0234518 A1 | 9/2008 | Sommer et al. |

OTHER PUBLICATIONS

Kirk-Othmer Encyclopedia Chem. Techn., New York, 2, pp. 338-348 (1978) by M.V. Moore.

* cited by examiner

METHOD FOR TREATING A SUBSTANCE MIXTURE COMPRISING AN AROMATIC AMINE, IN PARTICULAR A SUBSTANCE MIXTURE OF RAW ANILINE

CROSS-REFERENCE TO RELATED APPLICATIONS

This application is a National Phase application to PCT/EP2013/058898, filed Apr. 29, 2013 and European Application No.: 12166832.1 filed May 4, 2012.

FIELD OF THE INVENTION

The present invention relates to a process for treating a substance mixture comprising an aromatic amine, wherein the substance mixture is a first substance mixture and comprises an aromatic amine and compounds having a higher boiling point than the aromatic amine, comprising the step of: I) Distillatively separating the first substance mixture in a first distillation unit to separate off at least some of the aromatic amine and to additionally obtain a first bottom product, this first bottom product being discharged from the first distillation unit. This bottom product can then be diluted with wastes generated in any case in the manufacturing operation which makes it possible to reduce the loss of aromatic amines in the bottom product. In accordance with the invention, the aromatic amine is aniline or 2,4-diaminotoluene, preferably aniline.

BACKGROUND

Aromatic amines are important intermediates which need to be produced inexpensively and in large volumes. Production plants for aromatic amines are therefore generally built for very large capacities. The high productivity of these plants is ensured by very long reaction cycles and uninterrupted running between the start-up and shut-down procedures of the hydrogenation for regenerating the hydrogenation catalysts employed.

The main field of application of 2,4-diaminotoluene is the production of toluene diisocyanate (TDI). It is produced industrially by the hydrogenation of 2,4-dinitrotoluene.

The main field of application of aniline is the production of methylenediphenyldiamine (MDA) which is used to produce methylenediphenyldiisocyanate (MDI). Aniline is generally produced on an industrial scale by catalytic hydrogenation of nitrobenzene with hydrogen. It is particularly preferable to conduct the reaction as described in EP 0 944 578 A2 (isothermal mode of operation) and in EP 0 696 574 B1, EP 0 696 573 B1 and EP 1 882 681 A1 (adiabatic mode of operation). The production of MDA is described in numerous patents and publications (see, for example, H. J. Twitchett, Chem. Soc. Rev. 3(2), 209 (1974), M. V. Moore in: Kirk-Othmer Encycl. Chem. Technol., 3rd. Ed., New York, 2, 338-348 (1978)).

What is common to the described isothermal processes for producing aniline is that the starting material nitrobenzene is vaporized at elevated temperature in the hydrogen stream.

The reaction is generally conducted such that the gaseous nitrobenzene/hydrogen mixture is passed into the hydrogenation reactor and reacted here over the fixed-bed catalyst, optionally with a downstream post-reactor, at elevated temperature and atmospheric pressure.

The heat of reaction liberated is removed from the reactor via a heat exchanger and generally used for steam generation.

The reaction products aniline and water exit the reactor in gaseous form and are condensed out of the hydrogen stream via multistage condensation. The excess hydrogen is recirculated, supplemented with fresh hydrogen and again vaporized together with nitrobenzene and passed into the hydrogenation reactor as a mixture.

The hydrogen becomes loaded with gaseous impurities on account of the recirculating mode of operation. To remove these impurities, a substream is withdrawn from the hydrogen circuit and incinerated in the thermal exhaust air purification step.

The condensed-out reaction products separate into an organic phase (crude aniline) and an aqueous phase (aniline water) and these are subjected to further processing separately. The crude aniline also comprises water and organic by-products in dissolved form which are separated off by distillation.

Initially, a column is used to distil off the low-boiling secondary components (for example cyclohexylamine, cyclohexanone, benzene) overhead and the water in the sidestream as an aniline-water azeotrope. The sidestream is biphasic and is recycled into the abovementioned phase separation.

The low-boiling secondary components which also comprise aniline are drawn off at the top of the column and can either be disposed of directly in an incineration plant or initially condensed and later incinerated together with other residues.

The bottom product (aniline+high-boilers) is freed of the high-boiling by-products (for example N-cyclohexylaniline, N,N-diphenylamine, phenol) in a second distillation column. The pure aniline is distilled off overhead. The high-boilers accumulate in the bottom and are further concentrated in a third distillation column (residue column).

Aniline is recovered at the top of the residue column and fed back into the second column together with the bottom product of the first column. The bottoms from the residue column are transferred into a residue container. Here, a residual aniline content serves as solvent to maintain the pumpability of the residue. In addition, the residue is stored at elevated temperature to avoid precipitates or excessively high viscosities. The high-boilers together with the diluent residual aniline are supplied from the residue container to an incineration step.

The water separated in the phase separation is freed of the dissolved aniline by distillation and fed as wastewater into the biological wastewater treatment plant of the site. The aniline is distilled off as an azeotrope with water and is recycled into the abovementioned phase separation.

All stages of the process for producing aniline are carried out in a continuous operating mode.

The performance of a process for hydrogenating aromatic nitro compounds is defined by the quality of the product. The performance of a hydrogenation process is also defined by the ability to operate the entire process continuously without significant production outages. The shutting down of the hydrogenation, the regeneration of the hydrogenation catalyst and the starting up again of the hydrogenation process are generally referred to as a smooth sequence of events in the hydrogenation cycle.

Since all stages of the process for producing aniline are carried out in a continuous operating mode during the hydrogenation cycle, it is also necessary to operate the work-up of crude aniline without interruption. Lastly, it is also important to achieve a high yield of the desired product which means avoiding by-products in the reaction and minimizing production losses in the plant. Such losses arise in the distillation of the product for example, since concentrating the high-boiling secondary components in the bottom is possible only to a certain extent without the residue solidifying or parts thereof precipitating and forming undesired precipitates. A significant proportion of product is therefore always incinerated with the secondary components.

EP 0 794 170 A1 discloses a process for separating off high-boilers in the production of diaminotoluene. The crude dewatered diaminotoluene is passed into a distillation unit comprising a packed column having a continuous evaporator for the column bottom. In one embodiment, (FIG. 1) the packed column has a falling-film evaporator arranged downstream of it into which the bottom discharge of the packed column is passed. In another embodiment (FIG. 2), a falling-film evaporator is arranged upstream of the packed column. Here, the packed column is fed from the vapors of the falling-film evaporator. In both cases, the falling-film evaporator is intended to ensure that very little of the product of value (meta-diaminotoluene) is lost together with the high-boiling residues. In both cases, the bottom product of the falling-film evaporator (consisting essentially of high-boiling residues) is mixed with a condensed ortho-diaminotoluene stream withdrawn in the upper part of the packed column.

EP 0 696 574 B1 discloses in examples 9 and 10 a process in which the product of nitrobenzene hydrogenation including the water of reaction is distilled in a distillation column and the bottom product of the distillation column is diluted with the aniline-rich phase obtained after phase separation of the condensate of the top product of the same distillation column.

EP 1 005 888 B1 describes a rinsing apparatus for removing residues from the bottoms outlet of an evaporation apparatus and the use of said rinsing apparatus for the distillative work-up of salt-containing solutions. It is a disadvantage that the used rinsing agent again entails a certain cost and inconvenience to the extent that it needs to undergo costly incineration. Moreover, such a rinsing apparatus is unsuitable when high temperatures prevail at the bottom of the column and therefore high-boiling solvents would need to be used or the bottom would need to be cooled in order to carry out the rinsing operation without vaporization of the rinsing agent. In the process described, preference is given to using water, which, however, is only of limited suitability as a washing agent for organic residues. In addition, it is not always possible in practice to avoid washing agent entering the column and impairing the quality of the top product and/or the further work-up of the top product.

SUMMARY

It is therefore an object of the present invention to provide a process which ensures smooth operation of the work-up columns and simultaneously minimizes aniline losses.

This object is achieved in accordance with the invention by a process for treating a substance mixture comprising an aromatic amine, wherein the aromatic amine is aniline or 2,4-diaminotoluene,
wherein the substance mixture is a first substance mixture and comprises an aromatic amine (namely aniline or 2,4-diaminotoluene) and compounds having a higher boiling point than the aromatic amine, wherein the first substance mixture has preferably been dewatered, wherein the dewatering can be effected by phase separation and/or distillation, comprising the step of:

I) distillatively separating the first substance mixture in a first distillation unit to separate off at least some of the aromatic amine and to additionally obtain a first bottom product, this first bottom product being discharged from the first distillation unit;
wherein once discharged the bottom product from the first distillation unit is diluted with a condensed top product from a distillation unit distinct from the first distillation unit and/or with a composition comprising methanol.

It is an advantage of this procedure according to the invention that, on account of the dilution effect, the concentration of the desired aromatic amine in the residue (bottom product from the first distillation unit) can be reduced since the amine is no longer required as solvent. The high-boiling residues can therefore be concentrated further in the bottom of the column and the amine yield can thus be increased. In addition, energy-intensive heating of a residue container and the usual trace heaters for pipes can be dispensed with.

DETAILED DESCRIPTION

For the purposes of the present invention, a "distillation unit" comprises a distillation column and the accompanying peripheral devices such as evaporators for example, it also being possible for the distillation column to have an integrated evaporator. The first distillation unit can be a purifying distillation column for example, in particular an aniline purifying distillation column. Furthermore, the first distillation unit can also be employed in an integrated system with other distillation units, therefore being configured as a high-boiler column at the end of a multistage distillation. Although the demands on such a high-boiler column are higher on account of the physical constraints (vacuum, temperature, viscosity), advantages follow therefrom since the total mass flow of aromatic amine is no longer distilled in the column and the more technically complex apparatuses can therefore be made smaller.

The bottom product is advantageously discharged into a container and then diluted there. However, it is also conceivable for the dilution to take place in a pipeline located outside the first distillation unit.

The condensed top product from a distillation unit can be obtained from the first distillation unit and/or from a distillation unit distinct from the first distillation unit.

The residue (bottom product) is kept liquid by the remaining amine and also by sufficient additionally introduced diluents (composition comprising methanol and/or low-boilers obtained as top product from distillation units distinct from the first distillation unit). This also prevents blockages in the pipeline and in the lances for an incinerator. The balance is correct since the composition comprising methanol and/or the low-boilers which, in particular, originate from an integrated polyisocyanate system (for example an MDA operation) and need to be disposed of in any case now facilitate the amine recovery. For the purposes of the present invention, the term "low-boiler" preferably describes substances or substance mixtures having a boiling point at 1013 mbar of from ≥30° C. to ≤220° C., preferably from ≥50° C. to ≤197° C., more preferably from ≥50° C. to ≤185° C., most preferably from ≥60° C. to <100° C.

Other conceivable sources for this diluent liquid are low boilers separated off from the amine distillation, aliphatics-rich waste streams from the nitrobenzene process (cf. DE 10 2009 005324 A1) and low boilers separated-off from a TDA process (for example 1,3-diamino-4-methylcyclohexane).

Admixing low-boilers and/or methanol water (for example from the production of MDA) in the residue container to dilute the residue (bottom product from the first distillation unit), gives rise to the following advantages:
i) The dilution effect makes it possible to reduce the amine concentration of the residue.
ii) The high-boiling residues can therefore be concentrated further in the bottom of the column and the amine yield can thus be increased.
iii) The residue is kept liquid by sufficient low-boilers and/or methanol which stops the lances of a thermal exhaust air purifier (TAP) clogging.
iv) There is an additional energy saving because the residue can be stored at a lower temperature and trace heaters for pipes can be omitted.
v) The disposal balance is correct since use is made of liquids which in any case need to be disposed of.
vi) Since the dilution is only effected a residue container, the distillation is not impaired.

Embodiments of the present invention are described hereinafter. They can be combined as desired, unless the contrary is unambiguously evident from the context.

Even when the production of aromatic amines by gas phase hydrogenation is mentioned hereinbelow as an example, the process according to the invention can of course be applied to any substance mixture which comprise aromatic amines and are produced differently, i.e., in particular also to substance mixtures which comprise aromatic amines and are produced in liquid phase processes or those in which the input materials are reacted over catalyst fluidized beds.

In one embodiment of the process according to the invention, said process further comprises the steps Ia) and Ib), wherein Ia) and Ib) are carried out prior to I):
Ia) providing a second substance mixture, wherein the second substance mixture comprises the aromatic amine, compounds having a lower boiling point than the aromatic amine and compounds having a higher boiling point than the aromatic amine and the aromatic amine content is different from the aromatic amine content in the first substance mixture;
Ib) distillatively separating the second substance mixture in an upstream distillation unit to separate off compounds having a lower boiling point than the aromatic amine as top product and to additionally obtain the aromatic amine as sidestream and the first substance mixture as bottom product. The substance mixture to be treated in the process according to the invention is obtained as bottom product which of course also comprises the aromatic amine. In this case, the first distillation unit of the process according to the invention is preferably a residue column.

In a further embodiment of the process according to the invention, said process further comprises the steps IIa), IIb) and III), wherein IIa) and IIb) are carried out prior to III) and III) is carried out prior to I):
IIa) providing a second substance mixture, wherein the second substance mixture comprises the aromatic amine, compounds having a lower boiling point than the aromatic amine and compounds having a higher boiling point than the aromatic amine and the aromatic amine content is different to the aromatic amine content in the first substance mixture;
IIb) distillatively separating the second substance mixture in a second distillation unit to separate off compounds having a lower boiling point than the aromatic amine as top product and to additionally obtain a bottom product comprising the aromatic amine;
III) distillatively separating the bottom product from the second distillation unit in a third distillation unit to separate off at least some of the aromatic amine as top product and to additionally obtain the first substance mixture as bottom product.

Consequently, the sequence of steps in this embodiment is as follows: IIa), IIb), III), I). It is also evident that the designations "first distillation unit", "second distillation unit" and "third distillation unit" do not represent a sequence of the distillation units in the process according to the invention. On the contrary, the second distillation unit can be a low-boiler column, followed by the third distillation unit as an amine purifying column (in particular an aniline purifying column), to which is connected the first distillation unit as a high-boiler column.

In a preferred embodiment of the process according to the invention, the content of the aromatic amine in the bottom product from the first distillation unit is ≥5% by weight to ≤70% by weight, more preferably ≥10% by weight to ≤45% by weight, in each case based on the total weight of the bottom product. This is understood to mean the content of the aromatic amine in the bottom product once the bottom product has been discharged and before the bottom product is diluted.

In accordance with the invention, once discharged the bottom product from the first distillation unit is diluted with the top product from a distillation unit distinct from the first distillation unit and/or with a composition comprising methanol. In a preferred embodiment of the process according to the invention, once discharged the bottom product from the first distillation unit is diluted with the top product from a distillation unit distinct from the first distillation unit and/or with the composition comprising methanol such that the mixture obtained has a dynamic viscosity at 20° C. of from ≥0.3 mPas to ≤1000 mPas, preferably from ≥0.5 mPas to ≤100 mPas, more preferably from ≥1 mPas to ≤50 mPas, most preferably from ≥1 mPas to ≤10 mPas. Here, the viscosity is measured by means of a falling-ball viscosimeter according to DIN 53015/ISO 12058.

It is preferable for the condensed top product from the distillation unit distinct from the first distillation unit to be monophasic at the temperature at which the bottom product from the first distillation unit is diluted once discharged, i.e., to comprise water only up to the saturation limit, in order that spontaneous demixing into an aqueous phase and an organic phase is avoided. In this way, the diluted bottom product from the first distillation unit preferably also remains monophasic. In a further embodiment of the process according to the invention, the condensed top product from the distillation unit distinct from the first distillation unit therefore preferably comprises ≥80% by weight to ≤100% by weight of low boilers and ≥0% by weight to ≤20% by weight of water based on the total weight of the top product. It is particularly preferable for the condensed top product to consist of the aforementioned proportions of low-boilers and water.

In a further embodiment of the process according to the invention, the composition comprising methanol is a composition comprising methanol and water which has been obtained from a process for producing methylenediphenyldiamine (MDA).

The composition known as methanol water is generated in the production of MDA. The plants for producing aniline and MDA are commonly very close to one another since they are part of the chain of production of MDI. The transport path of methanol water from MDA to aniline is therefore very short and can be accomplished via a pipeline. Methanol water is generated in the reaction of the MDA process.

EP 1 616 890 A1 describes the acidic condensation of aromatic amines and formaldehyde to give MDA. In the absence of an acidic catalyst, formaldehyde initially undergoes condensation—industrially useable formaldehyde contains methanol for stabilization—with aniline to give what is known as an aminal and water. The rearrangement to give MDA is effected by acid catalysis in a first step to give para- and ortho-aminobenzylaniline. The aminobenzylanilines rearrange to give MDA in a second step. Following the reaction to give the aminal, initially at least some of the water and all of the methanol is removed from the aminal as so-called methanol water and the aminal is subsequently admixed with acidic catalyst and the acidic reaction mixture thus obtained is reacted further at temperatures of from 20° C. to 100° C. Here, the water content is between 0% by weight and 20% by weight.

In a further embodiment of the process according to the invention, the composition comprising methanol comprises ≥20% by weight to ≤95% by weight of methanol based on the total weight of the composition comprising methanol. It is preferable for the proportion to be ≥50% by weight to ≤80% by weight of methanol based on the total weight of the composition comprising methanol. It is further preferable for the remainder of the composition to comprise water and technically unavoidable impurities, in particular salts etc.

In a further embodiment of the process according to the invention, the flow rate of the composition comprising methanol is chosen such that the theoretical flow rate of pure methanol is ≥30% by weight based on the flow rate of discharged bottom product from the first distillation unit. This flow rate is preferably ≥40% by weight.

In a further embodiment of the process according to the invention, it can be preferable to use only one composition comprising methanol to dilute the bottom product from the first distillation unit, i.e., to completely dispense with supplying the condensed top product of another distillation unit. This can be the case in particular when a sufficient amount of a composition comprising methanol can be provided from an adjacent MDA plant. This embodiment can also be preferable when adding the condensed top product of another distillation unit would lead to a spontaneous phase separation of the diluted bottom product from the first distillation unit.

In a further embodiment of the process according to the invention, the bottom product from the third distillation unit is incinerated once it has been diluted.

BRIEF DESCRIPTION OF THE DRAWINGS

The present invention is more particularly described by the figures and examples which follow, but without being restricted thereto.

DETAILED DESCRIPTION OF THE DRAWINGS

Figure 1:
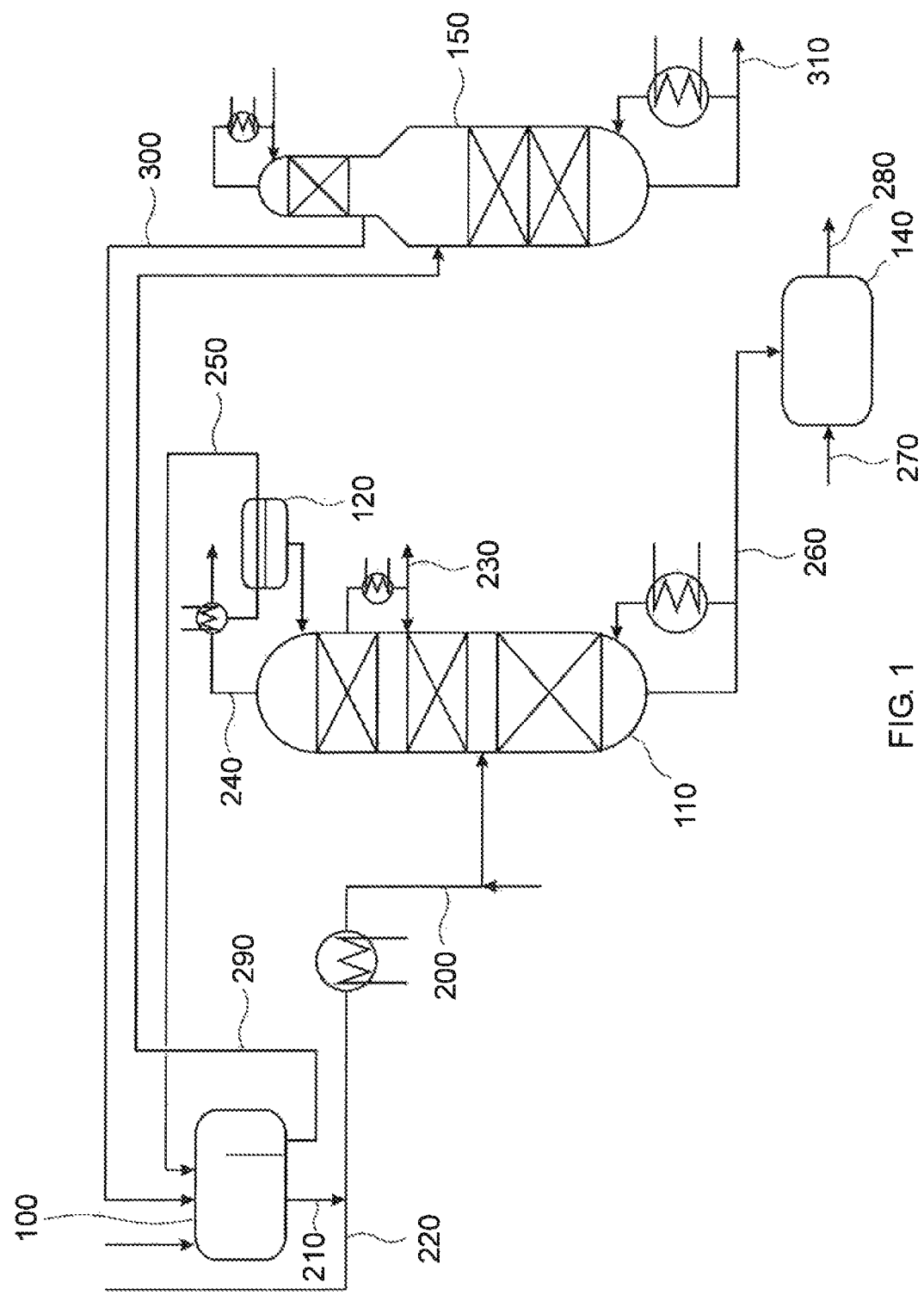
FIG. 1 is a schematic diagram of a plant and a process for working up the crude product from an aniline production process.

In the process scheme according to FIG. 1, crude aniline arrives in a first distillation unit 110, which is configured as an aniline purifying distillation column, either directly from a production plant/intermediate storage means (material stream 200) and/or from a phase separation container 100 (material stream 210). An aqueous base, preferably aqueous sodium hydroxide solution, (material stream 220) can also be added if required. The purifying distillation column 110 is operated at reduced pressure; the necessary vaporization energy can be supplied via continuous evaporators heated with steam. The necessary reduced pressure is established with a liquid ring pump. Aniline water serves as the operating liquid for the vacuum pumps.

Some of the pure aniline is introduced to the column as reflux using pure aniline pumps. The remainder is discharged as product once cooled down (material stream 230).

Low-boiling distillation products are withdrawn from the column 110 as top stream 240 and some of them are condensed. The organic, aniline-rich part of the condensate is returned to the top of the column via a phase separator 120. The aqueous part of the condensate is passed back into the phase separation container 100 as material stream 250.

The concentrated high-boilers remain in the column bottom. They are discharged as material stream 260 and collected in the residue receiver 140. Here, they are diluted with methanol water from an MDA operation (material stream 270) and sent for thermal disposal optionally together with low boilers (material stream 280).

The aqueous phase separated in the phase separation container 100 comprises dissolved aniline and is introduced as material stream 290 to a distillation unit configured as a stripping column 150. The top product from this distillation comprises an azeotrope of water and aniline and can then be recycled to the phase separation container 100 as material stream 300. At the bottom of the column, water largely freed of aniline is withdrawn from the process as waste water (material stream 310).

Figure 2:
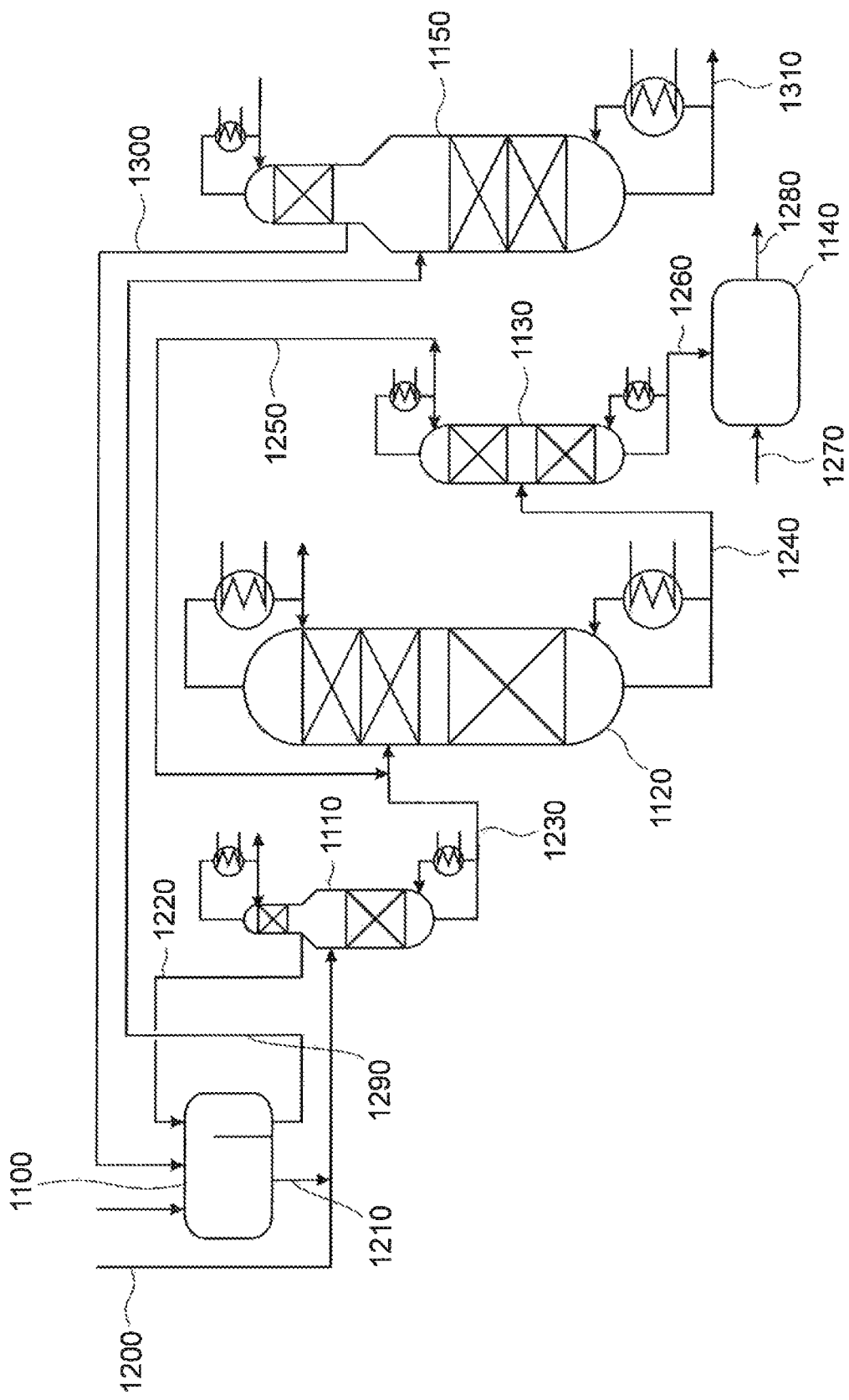
FIG. 2 is a schematic diagram of a further plant and a further process for working up the crude product from an aniline production process.

In the process scheme according to FIG. 2, crude aniline arrives in a column, which is described in the language of the invention as second distillation unit 1110 and which serves as a distillation column or dewatering column to separate off low-boilers, either directly from a production plant/intermediate storage means (material stream 1200) and/or from a phase separation container 1100 (material stream 1210). The dewatering column 1110 is operated at atmospheric pressure. The necessary vaporization energy can be supplied via a continuous evaporator heated with steam. A water/aniline azeotrope accumulates on the middle column trays and a mixture of water, aniline and low boilers accumulates at the top of the column. The top product is recycled to the top of the column after condensation in condensers and uncondensed fractions are disposed of as flue gas.

The water/aniline azeotrope is withdrawn from column 1110 as sidestream 1220 and recycled to the separation container 1100 for phase separation.

The crude aniline at the column bottom of the column 1110 has been largely freed of low boilers and water and is supplied as material stream 1230 to a further column described in the language of the invention as third distillation unit 1120 and further fractionated there. Aniline accumulates at the top of this purifying distillation column 1120 and the high-boilers accumulate in the bottoms. The pure aniline vapors from the top of the column are condensed out.

The purifying distillation column 1120 is operated at reduced pressure; the necessary vaporization energy can be supplied via continuous evaporators heated with steam. Some of the pure aniline collected is introduced to the top of the column as reflux using pure aniline pumps.

The bottoms of the purifying distillation column 1120 that are enriched with high boilers are conveyed as material stream 1240 into the column configured as residue column 1130 and described in the language of the invention as first distillation unit (residue distillation) for further concentration. The residue column 1130 likewise operates at reduced pressure. The necessary vaporization energy can be supplied via a falling-film evaporator heated with steam. At the top of the column, aniline vapor passes over and is condensed out in a condenser. Some of the condensate is introduced to the top of the column as reflux using distillate pumps. Depending on quality, the remaining condensate can either be discharged via a heat exchanger or admixed with the feed stream of the pure aniline column 1120 as material stream 1250.

The concentrated high-boilers remain in the column bottom. They are discharged as material stream 1260 and collected in the residue receiver 1140. Here, they are diluted with methanol water from an MDA operation (material stream 1270) and sent for thermal disposal (material stream 1280) optionally together with further low-boilers.

The aqueous phase separated in the phase separation container 1100 comprises dissolved aniline and is introduced as material stream 1290 to a fourth distillation unit configured as a stripping column 1150. The top product from this distillation comprises an azeotrope of water and aniline and can then be recycled to the phase separation container 1100 as material stream 1300. At the bottom of the column, water largely freed of aniline is withdrawn from the process as waste water (material stream 1310).

EXAMPLES

Example 1 (Comparative Example)

Normal Aniline Loss (328 Metric Tons Per Year)

A work-up apparatus connected to an aniline process and comprising a low-boiler column, a pure aniline column and a residue column was operated such that (FIG. 2) a residual aniline content of about 50% was established in the bottom of the residue column (1130, first distillation unit). The residue discharged from the bottom was stored at 35° C. and subsequently disposed of by incineration. The relevant characteristic data are reproduced in table 1.

TABLE 1

| Flow rate of aniline to the residue column (stream 1240) | Proportion of high-boilers | Discharge from bottom (1260) | Aniline loss |
|---|---|---|---|
| 800 kg/h | 5% | 80 kg/h | 40 kg/h |

Example 2 (Comparative Example)

Reduced Aniline Loss (Theoretically 56 Metric Tons Per Year) with Blockage of the Pipeline and Lances in the TAP A work-up apparatus connected to an aniline process and comprising a low-boiler column, a pure aniline column and a residue column is operated such that (FIG. 2) a residual aniline content of 30% is established in the bottom of the residue column. The residue discharged from the bottom was stored at 120° C. and subsequently disposed of by incineration. Here, despite trace heating of the pipeline to the incinerator, deposits in this pipeline and blockages in the lances of the incineration plant occurred. Frequent interruption of the process was necessary in order to clean both a dirt trap disposed on the suction side of the residue pump and the lance in the incineration plant. The residue container heating was turned off during these cleaning operations. On cooling of the residue mixture an increase in viscosity occurred which led to the mixture no longer being pumpable. The relevant characteristic data are reproduced in table 2.

TABLE 2

| Flow rate of aniline to the residue column (stream 1240) | Proportion of high-boilers | Discharge from bottom (1260) | Aniline loss |
|---|---|---|---|
| 800 kg/h | 5% | 57 kg/h | 17 kg/h |

Example 3 (Inventive Example)

Dilution of the Residue in the Container with Methanol

A work-up apparatus connected to an aniline process and comprising a low-boiler column, a pure aniline column and a residue column was operated such that (FIG. 2) a residual aniline content of about 30% by weight was established in the bottom of the residue column. The residue discharged from the bottom was stored at 35° C. and diluted with about an 0.6-fold amount (mass flow), based on the residue discharged, of methanol water (72% by weight of methanol) from an adjacent methylenediphenyldiamine (MDA) operation. There were no problems with blockages or deposits on disposal of the residue thus treated. The relevant characteristic data are reproduced in table 3.

TABLE 3

| Flow rate of aniline to the residue column (stream 1240) | Proportion of high-boilers | Discharge from bottom (1260) | Addition of methanol water (1270) | Aniline loss |
|---|---|---|---|---|
| 800 kg/h | 5% | 57 kg/h | 35 kg/h | 17 kg/h |

What is claimed is:

1. A process for treating a substance mixture comprising an aromatic amine, wherein said aromatic amine comprises aniline or 2,4-diaminotoluene,
    wherein the substance mixture is a first substance mixture and comprises an aromatic amine and compounds having a higher boiling point than the aromatic amine, comprising:
    I) distillatively separating said first substance mixture in a first distillation unit to separate off at least some of said aromatic amine and to additionally obtain a first bottom product, with said first bottom product being discharged from said first distillation unit;
    wherein once discharged said bottom product from said first distillation unit is diluted with a condensed top product from a distillation unit which is distinct from said first distillation unit and/or with a composition comprising methanol; wherein said condensed top product originating from a distillation unit which is distinct from said first distillation unit comprises ≥80% by weight to <100% by weight of low-boilers and ≥0% by weight to <20% by weight of water, and wherein the content of said aromatic amine in said bottom product from said first distillation unit (110, 1130) is ≥5% by weight to ≤70% by weight, based on the total weight of the bottom product.

2. The process as claimed in claim 1, further comprising steps Ia) and Ib), wherein Ia) and Ib) are carried out prior to I):

Ia) providing a second substance mixture, wherein the said second substance mixture comprises said aromatic amine, compounds having a lower boiling point than said aromatic amine and compounds having a higher boiling point than said aromatic amine and the aromatic amine content is different from the aromatic amine content in said first substance mixture;

Ib) distillatively separating said second substance mixture in an upstream distillation unit to separate off compounds having a lower boiling point than said aromatic amine as top product and to additionally obtain said aromatic amine as sidestream and said first substance mixture as bottom product.

3. The process as claimed in claim 1, further comprising steps IIa), IIb) and III), wherein IIa) and IIb) are carried out prior to III) and III) is carried out prior to I):

IIa) providing a second substance mixture, wherein said second substance mixture comprises said aromatic amine, compounds having a lower boiling point than said aromatic amine and compounds having a higher boiling point than said aromatic amine and the aromatic amine content is different from the aromatic amine content in said first substance mixture;

IIb) distillatively separating said second substance mixture in a second distillation unit to separate off compounds having a lower boiling point than said aromatic amine as top product and to additionally obtain a bottom product comprising said aromatic amine;

III) distillatively separating said bottom product from said second distillation unit in a third distillation unit to separate off at least some of said aromatic amine as top product and to additionally obtain said first substance mixture as bottom product.

4. The process as claimed in claim 1, wherein once discharged said bottom product from said first distillation unit is diluted with said top product from a distillation unit distinct from said first distillation unit and/or with said composition comprising methanol such that the mixture obtained has a viscosity at 20° C. of from ≥0.3 mPas to ≤1000 mPas.

5. The process as claimed in claim 1, wherein said composition comprising methanol is a composition comprising methanol and water which has been obtained from a process for producing methylenediphenyldiamine.

6. The process as claimed in claim 1, wherein said composition comprising methanol comprises ≥20% by weight to ≤95% by weight of methanol.

7. The process as claimed in claim 1, wherein the flow rate of said composition comprising methanol is chosen such that the theoretical flow rate of pure methanol is ≥30% by weight based on the flow rate of discharged bottom product from said first distillation unit.

8. The process as claimed in claim 1, wherein once discharged said bottom product from said first distillation unit is diluted only with one composition comprising methanol.

9. The process as claimed in claim 1, wherein said bottom product from said first distillation unit is incinerated once it has been diluted.

* * * * *